(12) United States Patent
Rivier et al.

(10) Patent No.: US 12,711,347 B2
(45) Date of Patent: Aug. 18, 2026

(54) MEDICAL CONTAINER, SYSTEM AND METHOD FOR TRACKING DATA RELATING TO SAID MEDICAL CONTAINER

(71) Applicant: Becton Dickinson France, Le Pont de Claix (FR)

(72) Inventors: Cédric Rivier, Voreppe (FR); Nicolas Euvrard, London (GB); Alfred Leibbrand, Claix (FR)

(73) Assignee: Becton Dickinson France, Le Pont-de-Claix (FR)

( * ) Notice: Subject to any disclaimer, the term of this patent is extended or adjusted under 35 U.S.C. 154(b) by 149 days.

(21) Appl. No.: 18/270,761

(22) PCT Filed: Jan. 4, 2022

(86) PCT No.: PCT/EP2022/050059
§ 371 (c)(1),
(2) Date: Jul. 3, 2023

(87) PCT Pub. No.: WO2022/148741
PCT Pub. Date: Jul. 14, 2022

(65) Prior Publication Data
US 2024/0058521 A1 Feb. 22, 2024

(30) Foreign Application Priority Data
Jan. 5, 2021 (EP) .................................... 21305009

(51) Int. Cl.
*G06K 19/08* (2006.01)
*G06K 19/07* (2006.01)
(Continued)

(52) U.S. Cl.
CPC ......... *G06K 19/083* (2013.01); *G06K 19/072* (2013.01); *G06K 19/0724* (2013.01);
(Continued)

(58) Field of Classification Search
CPC ............... G06K 19/083; G06K 19/072; G06K 19/0724; G06K 17/0025; A61M 5/002;
(Continued)

(56) References Cited

U.S. PATENT DOCUMENTS 8,945,066 B2 * 2/2015 Bochenko .............. G16H 10/60 604/189
2002/0008143 A1 1/2002 Bridgelall
(Continued)

FOREIGN PATENT DOCUMENTS

CN 107683415 A 2/2018
EP 3200142 A1 * 8/2017 ......... G06Q 30/0281
(Continued)

*Primary Examiner* — Tuyen K Vo
(74) *Attorney, Agent, or Firm* — The Webb Law Firm

(57) ABSTRACT

The disclosure relates to a medical container including a first RFID tag on and/or within the medical container. The first RFID tag being operable in a first frequency band and being configured for storing a unique identifier of the medical container; and at least one of (i) a second RFID tag on and/or within the medical container, the second RFID tag being operable in a second frequency band lower than the first frequency band and being configured for storing the unique identifier of the medical container; and (ii) an optical mark on and/or within the medical container, the optical mark encoding the unique identifier of the medical container.

17 Claims, 3 Drawing Sheets

(51) Int. Cl.
*A61M 5/00* (2006.01)
*A61M 5/32* (2006.01)

(52) U.S. Cl.
CPC .......... *A61M 5/002* (2013.01); *A61M 5/3202* (2013.01); *A61M 2205/6054* (2013.01)

(58) Field of Classification Search
CPC ......... A61M 5/3202; A61M 2205/6054; B01L 2300/022; B01L 3/5453; B01L 9/06
See application file for complete search history.

(56) References Cited

U.S. PATENT DOCUMENTS

2004/0089707 A1 5/2004 Cortina et al.
2005/0218219 A1* 10/2005 Sano .................. G06K 7/10128 235/383
2006/0051239 A1 3/2006 Massaro
2006/0291533 A1* 12/2006 Faries, Jr. ............. A61J 1/1462 374/E11.018
2007/0145150 A1 6/2007 Barczyk et al.
2010/0085166 A1 4/2010 Speich
2011/0093279 A1* 4/2011 Levine .................... G06F 16/24 235/375
2011/0201867 A1 8/2011 Wagner
2011/0205074 A1* 8/2011 Feng ................. A61M 5/16845 340/613
2011/0209212 A1 8/2011 Newlin et al.
2012/0100557 A1 4/2012 Fox et al.
2012/0130534 A1 5/2012 Wurm
2013/0048711 A1* 2/2013 Burns ................ G06K 7/10455 235/375
2014/0330685 A1* 11/2014 Nazzari ................ G06Q 10/083 705/28
2015/0209510 A1* 7/2015 Burkholz ................ G06F 3/011 604/93.01
2015/0356398 A1 12/2015 Morris
2016/0150760 A1 6/2016 Wang
2016/0259952 A1* 9/2016 Van Rens .......... G06K 7/10366
2018/0091317 A1* 3/2018 Sieh ....................... G06K 19/14
2018/0193552 A1* 7/2018 Wright ................ A61M 5/3158
2019/0139638 A1* 5/2019 Keefe .................... G16H 20/13
2020/0143218 A1* 5/2020 Lee ......................... H04W 4/80

FOREIGN PATENT DOCUMENTS

EP 3231467 A1 10/2017
EP 3293523 B1 10/2020
JP 2006295729 A 10/2006
JP 2008517389 A 5/2008
JP 2011123878 A 6/2011
KR 2020100000016 U 1/2010
KR 1020190017910 A 2/2019
WO 2006045395 A1 5/2006
WO 2010050210 A1 5/2010
WO 2018010931 A1 1/2018

* cited by examiner

MEDICAL CONTAINER, SYSTEM AND METHOD FOR TRACKING DATA RELATING TO SAID MEDICAL CONTAINER

CROSS-REFERENCE TO RELATED APPLICATIONS

This application is the United States national phase of International Application No. PCT/EP2022/050059 filed Jan. 4, 2022, and claims priority to European Patent Application No. 21305009.9 filed Jan. 5, 2021, the disclosures of which are hereby incorporated by reference in their entireties.

BACKGROUND OF THE INVENTION

Field of the Invention

The present disclosure relates to a medical container, and to a system and a method for tracking data relating to said medical container.

Description of Related Art

Medical containers are widely used in the pharmaceutical industry.

Said medical containers may be manufactured, for example by forming glass or plastics, filled with a pharmaceutical composition, sterilized, and transported before being used, for example for injecting the pharmaceutical composition to a patient or for transferring the pharmaceutical composition into another container.

For safety reasons, such medical containers require a strong traceability throughout their lifetime. Such a traceability may be intended to prevent mixing different batches, to determine on which line a faulty product has been manufactured, to find products concerned by a quality issue (e.g. in case of a product recall), to determine if the product has expired, and/or to make sure that the product is not counterfeited.

Solutions have been proposed to achieve traceability of the medical containers.

A first solution consists in marking the medical containers with a data tag or label. Each data tag differs from one container to the other, thereby making it possible to individually track each container.

The customer may ensure traceability at the container level, for example by using color labelling which may be quite difficult to implement, and/or by performing laborious manual procedures during line clearance or manual reconciliation of the containers. In particular, color labelling can be performed only on the external diameter of the container, close to the flange, and is very likely to be degraded during sterilization operations.

In addition, marking of the container is not visible when said container is contained in a packaging, for example for conveying during a processing step or for transportation. Hence, an operator cannot see the marking and cannot identify the containers, which severely limits the tracking of the containers.

A second solution consists in marking the packaging containing the medical containers instead of the medical containers themselves.

However, before the containers are arranged in the packaging, there is no traceability at the container level. Moreover, when an operator removes the medical containers from the packaging, for example for performing a quality check of said containers and/or filling them with a pharmaceutical composition, the traceability of the containers is lost.

SUMMARY OF THE INVENTION

There thus remains a need for a system and a method for tracking data for a medical container, which allows ensuring the traceability of the medical container throughout its lifetime, both in an industrial context and at a final point of use.

To that end, some embodiments relate to a medical container comprising:

- a first RFID tag on and/or within the medical container, the first RFID tag being operable in a first frequency band and being configured for storing a unique identifier of the medical container; and
- at least one of:
  - (i) a second RFID tag on and/or within the medical container, the second RFID tag being operable in a second frequency band lower than the first frequency band and being configured for storing the unique identifier of the medical container; and
  - (ii) an optical mark on and/or within the medical container, the optical mark encoding the unique identifier of the medical container.

Thanks to the at least two elements (RFID tag(s) and/or optical mark) storing and/or encoding the unique identifier (UDI) of the medical container according to different technologies, the unique identifier may be read by at least two different readers operating according to said technologies, which provides more versatility in the choice of a suitable reader depending on the processing step or location. Besides, since at least one of the elements is an RFID tag, the UDI may be read even if the medical container is not visible, for example when it is enclosed in a packaging, or hidden by a layer of packaging or any object in its vicinity.

In some embodiments, the first and second RFID tags are combined into a dual frequency RFID tag.

In other embodiments, the first and second RFID tags are distinct from each other.

In some embodiments, the first frequency band ranges from 860 to 960 MHz.

In some embodiments, the second frequency band is 13.56 MHz.

In some embodiments, the optical mark may comprise at least one of: a one-dimensional mark, such as a bar code; a two-dimensional mark such as a Data Matrix, a QR code, a Dotcode, a Direct Part Marking (DPM) code, or a random unique marking; and a text.

In some embodiments, (i) the first RFID tag and (ii) the second RFID tag or the optical mark may be located on a same part of the medical container.

Alternatively, (i) the first RFID tag and (ii) the second RFID tag or the optical mark may be located on different parts of the medical container.

In the present text, a part designates an object that can be provided as an independent physical entity. Accordingly, a barrel and a cap are different parts of a medical container.

Some embodiments relate to a system for tracking data relating to at least one such medical container. Said system may comprise:

- a first RFID tag on and/or within each medical container, the first RFID tag being operable in a first frequency band and being configured for storing the unique identifier of each respective medical container;

at least one of:

(i) a second RFID tag on and/or within each medical container, the second RFID tag being operable in a second frequency band lower than the first frequency band and being configured for storing the unique identifier of each respective medical container; and (ii) an optical mark on and/or within each medical container, the optical mark encoding the unique identifier of each respective medical container;

a data storage system configured for storing at least the unique identifier of each medical container.

In some embodiments, the data storage system may further be configured for storing data relating to the processing of each medical container, said data being associated with the UDI of each medical container.

In some embodiments, the system may further comprise:

at least one first RFID reader coupled to the data storage system and configured to read the first RFID tag of each medical container; and at least one of:

(i) a second RFID reader coupled to the data storage system and configured to read the second RFID tag of each medical container; and (ii) an optical reader coupled to the data storage system and configured to read the optical mark of each medical container.

Some embodiments relate to a method for tracking data relating to at least one such medical container. Said method may comprise:

generating the unique identifier of each medical container;

forming the first RFID tag on and/or within each medical container, wherein the first RFID tag stores the unique identifier of the respective medical container;

forming on and/or within each medical container at least one of the second RFID tag storing the unique identifier of the respective medical container or the optical mark encoding the unique identifier of the respective medical container;

storing the unique identifier of each medical container in a data storage system.

In some embodiments, forming the first and/or second RFID tag comprises at least one of: labelling, in-mold labelling, screwing, over-molding, direct antenna printing.

In some embodiments, forming the optical mark comprises at least one of: labelling, in-mold labelling, enamel sintering, inkjet printing, laser marking such as picosecond laser marking or femtosecond laser marking, drop-on demand printing, and dot peen marking.

In some embodiments, the method may further comprise:

(a) providing:

at least one first RFID reader coupled to the data storage system and configured to read the first RFID tag of each medical container; and at least one of:

(i) a second RFID reader coupled to the data storage system and configured to read the second RFID tag of each medical container; and (ii) an optical reader coupled to the data storage system and configured to read the optical mark of each medical container; and (b) reading at least one of the first RFID tag, the second RFID tag and the optical mark of at least one medical container with the first RFID reader, the second RFID reader and/or the optical reader and determining from the data storage system the unique identifier of said at least one medical container.

BRIEF DESCRIPTION OF THE DRAWINGS

Further features and advantages will be disclosed in the following detailed description, based on the appended drawings, wherein.

Reference signs identical from one figure to another one represent similar objects or parts, which may thus not being described again in detail.

Of course, the drawings are provided for sake of illustration only, and are not intended to limit the scope of the disclosure to the illustrated embodiments.

DESCRIPTION OF THE INVENTION

The medical container may be a syringe, a vial or a cartridge.

In general, the medical container may include a barrel adapted to contain a pharmaceutical composition and a cap covering a tip of the barrel. In some embodiments, the medical container may include a flange extending radially outwardly at an end of the barrel, opposite to the cap.

A plurality of such medical containers may be packaged together in a packaging, at different steps of the processing.

Such a packaging may comprise a plurality of layers that separate the containers from the outside environment. Some of said layers may be configured to form a barrier to air, fluids, and/or any contaminant that may affect the sterility of the containers. Some of said layers may be configured to protect the medical containers from shocks and/or vibrations that could affect their integrity. In the present text, the "first layer" designates a layer of the packaging that is closer to the medical containers. In particular, said first layer is in contact with the atmosphere that surrounds the medical containers. Said first layer is also, chronologically, one of the first layers used in the processing of the medical containers. Depending on the processing step, one or more layers of the packaging may not be present.

The first layer of the packaging may be a nest configured to maintain the at least one medical container in a determined position and/or orientation, or a tub containing such a nest. According to a preferred embodiment, the first layer is the nest.

Figure 1:
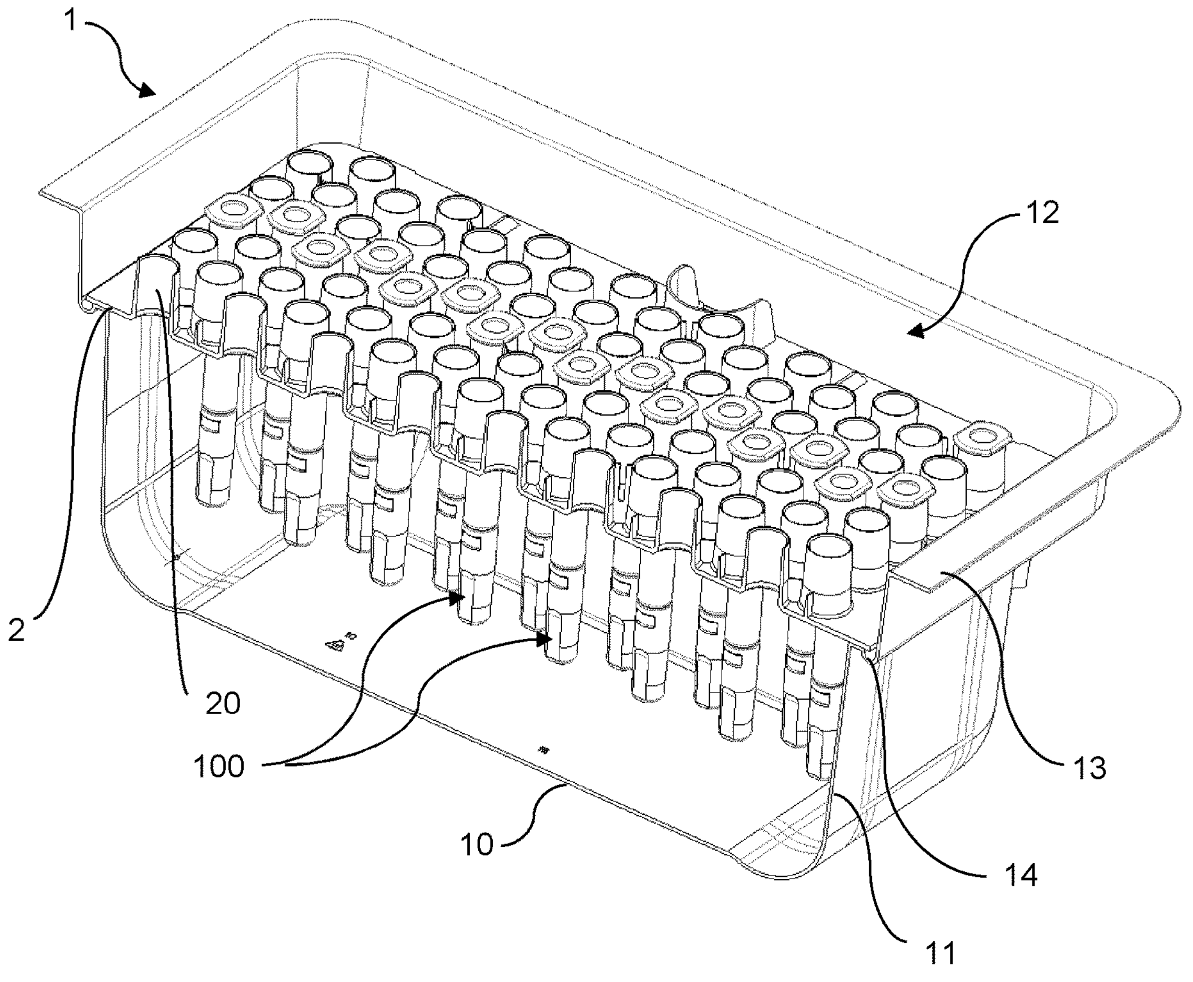
FIG. 1 is a partial cut of a packaging for medical containers comprising a nest and a tub.

FIG. 1 illustrates an embodiment of such a packaging.

The packaging comprises a tub 1, which is generally made of a plastic material, which is configured to enclose a plurality of medical containers 100. The tub may comprise a bottom 10, a peripheral wall 11 extending from the bottom to a top opening 12 of the tub. A peripheral flange 13 may extend outwardly from the top of the peripheral wall 11. The peripheral flange may be configured to be sealed to a sealing cover (not shown) to sealingly close the tub.

Advantageously, the medical containers 100 may be arranged vertically in the tub, i.e. the longitudinal axis of the barrel of the medical container extends in a vertical direction (which is the direction of gravity), with an opening of the barrel directed toward the top of the tub. In this orientation, the medical containers may thus be filled with a pharmaceutical composition while remaining in the tub, thereby minimizing handling of the medical containers.

To that end, the medical containers 100 may be placed in a nest 2, which comprises a plurality of guiding holes 20 configured to receive a respective medical container and maintain it in the vertical direction. The tub 1 may comprise a peripheral internal rim 14 configured to support the nest 2.

In other embodiments (not represented), the medical containers may be arranged in a different orientation in the tub, e.g. in a horizontal direction, but this orientation is less preferred since it does not allow filling the medical containers directly in the tub.

Figure 2:
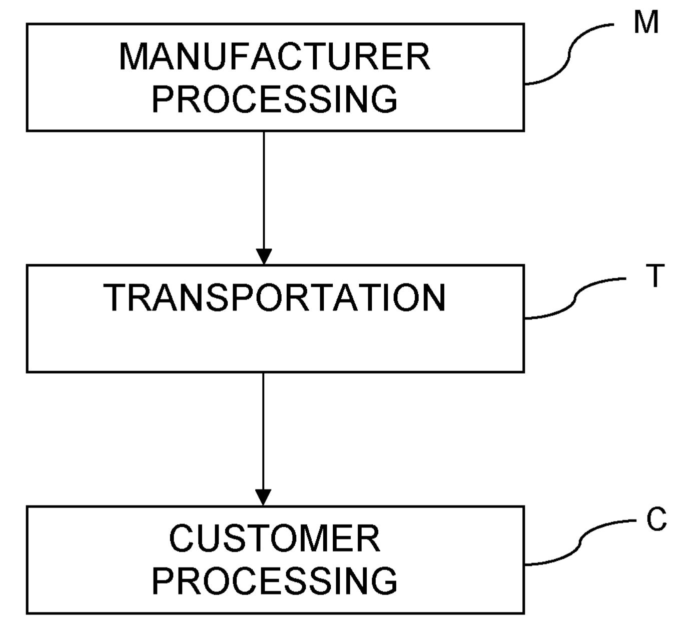
FIG. 2 illustrates a typical workflow of processing of medical containers.

The term "processing" refers to the steps involving the medical containers, from their manufacture by a manufacturer and their arrangement in the first layer of the packaging, to the final packaging by a customer after the medical containers have been inspected by the customer. A first part M of the processing, referred to as "manufacturer processing", may be performed by the manufacturer, and a second part C of the processing, referred to as "customer processing", may be performed by a customer or successively by a plurality of customers. The processing may also include the transportation T of the first layer of packaging containing the medical containers from the manufacturer to the customer (see FIG. 2). The steps performed in the manufacturer processing and those performed in the customer processing will be described in more details in the following text.

The present disclosure relates to systems and methods ensuring a clear and complete traceability of the medical containers from their manufacturing by the manufacturer and packaging in the first layer to the customer at a final packaging step, and even further up to the use and/or disposal of the medical containers.

Said traceability may be achieved by generating and associating a unique identifier to each medical container and by storing, in a data storage system, the UDI of each medical container along with data relating to the processing of said medical container.

A unique identifier is related and specific to each single syringe. A unique identifier related with one syringe is different from another unique identifier related with another syringe. Such a unique identifier may be a Unique Serial Number (USN) which will be preferably in keeping with GS1 standards, for example SGTIN-96 or GIAI-96 standards; or a unique device identifier (UDI). A UDI may be defined according to authorities' regulations, for instance EU 745/2027 or FDA-2017-D-6841.

To that end, at each processing step, the unique identifier of each medical container is read, and data relating to the processing step are written in the data storage system, in connection with the respective unique identifier. Thus, at any time, a user reading the unique identifier of the medical container may access to the data stored in the data storage system associated with said unique identifier.

Each medical container may comprise at least two elements storing or encoding the unique identifier of the medical container according to at least two different technologies. Said technologies include RFID technologies (with different ranges of frequencies being usable) and optical technologies (visual marks having a specific shape or pattern).

Among RFID technologies, UHF and NFC protocols are widely used. In both cases, an RFID tag comprises an RFID chip and an antenna connected to the chip. An RFID reader can read data (in particular the unique identifier) stored in a memory of the chip by communicating with the chip via the antenna at a suitable frequency.

UHF (acronym for Ultra High Frequency) corresponds to a frequency band ranging from 860 to 960 MHz. UHF readers are frequently used in industrial facilities.

Preferably, the unique identifier of the medical container complies with a standard, such as GS1 EPC Gen2, in order to facilitate interfacing the UHF tag of the medical container with all UHF readers that may be used along the manufacturing, processing and transportation of the medical container.

NFC (acronym for Near Field Communication) corresponds to a lower frequency band than UHF. More precisely, NFC corresponds to a frequency of 13.56 MHz. NFC readers are commonly used in consumer applications. In particular, NFC protocol may be embedded in a smartphone, which renders NFC tags particularly useful for reading the unique identifier at the point of use.

Each RFID tag may be provided in the form of a self-adhesive label, which can be adhered to the medical container, or in the form of a self-supported device that may be incorporated into the medical container, e.g. by overmolding. More generally, the RFID tag may be applied in or on the medical container by labelling, in-mold labelling, screwing, over-molding, and/or direct antenna printing.

In preferred embodiments, the optical mark may be a one-dimensional mark, such as a bar code; a two-dimensional mark such as a Data Matrix, a QR code, a Dotcode, a Direct Part Marking (DPM) code, or a random unique marking; or a text.

Such an optical mark may be formed in or on the medical container by at least one of the following processes: labelling, in-mold labelling, enamel sintering, inkjet printing, laser marking such as picosecond laser marking or femtosecond laser marking, drop-on demand printing, and dot peen marking. The optical mark may be implemented on a surface of the material of the medical container, or within the bulk material of the medical container. Preferably, the mark is implemented within the bulk material of the medical container, so as not being removable from the medical container.

Optical marks may be read by optical readers, such as bar code or QR code readers. Such optical readers may be embedded in a smartphone comprising a camera, which renders optical marks particularly useful for reading the unique identifier at the point of use. A limitation of optical marks, as compared to RFID tags, is line of sight, since the mark has to be accessible to the reader to enable reading the unique identifier.

Each medical container may thus comprise:

a first RFID tag on and/or within the medical container, the first RFID tag being operable in a first frequency band and being configured for storing the unique identifier of the medical container; and at least one of:

(i) a second RFID tag on and/or within the medical container, the second RFID tag being operable in a second frequency band lower than the first frequency band and being configured for storing the unique identifier of the medical container; and (ii) an optical mark on and/or within the medical container, the optical mark encoding the unique identifier of the medical container.

When both elements are RFID tags (e.g. UHF and NFC tags), both tags may be combined into a dual frequency RFID tag. Such dual frequency RFID tags are available on the market. Alternatively, said tags may be distinct from each other.

In some embodiments, both elements storing and/or encoding the unique identifier of the medical container (RFID tag(s) and/or mark) may be located on a same part of the medical container; for example, both elements may be located on or in a barrel, or both elements may be located on or in a cap of the medical container.

In other embodiments, at least two elements storing and/or encoding the unique identifier of the medical container (RFID tag(s) and/or mark) may be located on different parts of the medical container; for example, a first element may be located on or in a barrel, and a second element may be located on or in a cap of the medical container.

Figure 3:
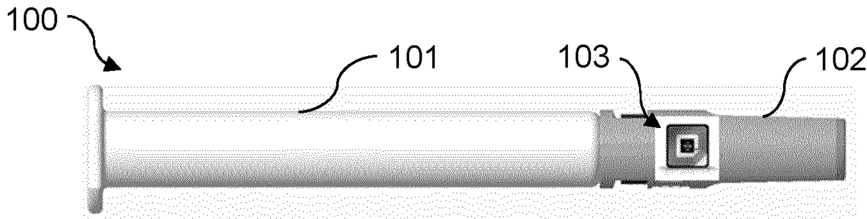
FIG. 3 represents a medical container according to a first embodiment, comprising a dual frequency RFID tag.

FIG. 3 illustrates a first embodiment of a medical container.

The medical container 100 comprises a barrel 101 and a cap 102 covering a tip of the barrel.

The medical container further comprises a dual frequency RFID tag 103 storing the unique identifier of the medical container. Preferably, said dual frequency RFID tags operates both in the UHF range and in the NFC range. In this way, the unique identifier of the medical container may be read by either an UHF reader (e.g. in industrial facilities) or an NFC reader (e.g. at point of use), using a single RFID tag. Said reading may be done even if the medical container is in the first layer of packaging, or hidden by an object located between the reader and the medical container.

In the illustrated embodiment, the tag 103 is located on the cap 102, but, in other embodiments, the tag 103 could be located on the barrel 101 or on any other part of the medical container 100.

Figure 4A:
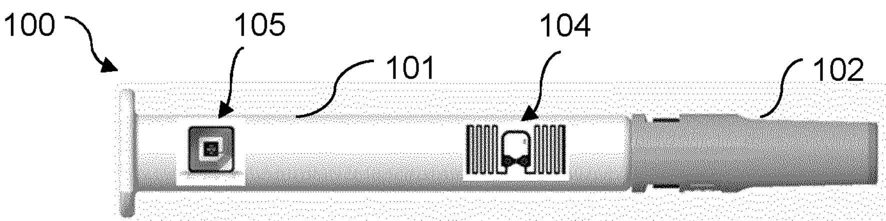
FIG. 4A represents a medical container according to a second embodiment, comprising an UHF RFID tag and an NFC RFID tag located on a same part of the medical container.

FIG. 4A illustrates a second embodiment of the medical container.

As in FIG. 3, the medical container 100 comprises a barrel 101 and a cap 102 covering a tip of the barrel.

The medical container further comprises a first RFID tag 104 (e.g. operating in the UHF range) and a second RFID tag 105 operating at a different frequency from the first RFID tag (e.g. in the NFC range).

In the illustrated embodiment, both tags 104 and 105 are located on the barrel 101, but, in other embodiments, both tags 104, 105 could be located on the cap 102 or on any other part of the medical container 100.

Figure 4B:
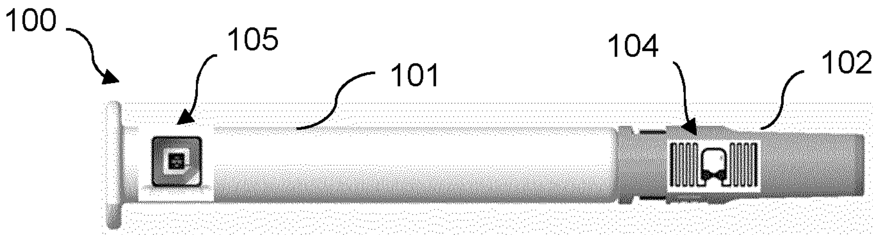
FIG. 4B represents a medical container according to a variant of the second embodiment, wherein the UHF RFID tag and the NFC RFID tag are located on different parts of the medical container.

FIG. 4B illustrates a variant of said second embodiment, wherein the first RFID tag 104 and the second RFID tag 105 are located on different parts of the medical container. For example, the first tag (UHF) may be located on the cap 102 and the second tag (NFC) may be located on the barrel 101, or conversely.

Figure 5:
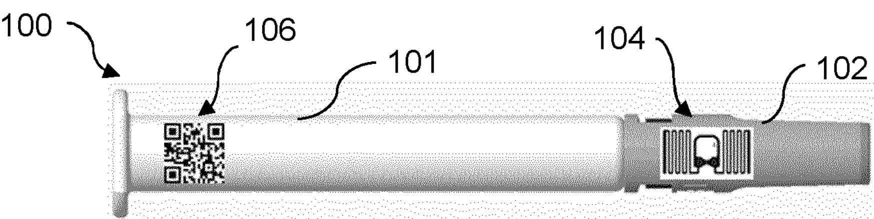
FIG. 5 represents a medical container according to a third embodiment, comprising an UHF RFID tag and an optical mark.

FIG. 5 illustrates a third embodiment of the medical container.

The medical container 100 comprises a barrel 101 and a cap 102 covering a tip of the barrel.

The medical container further comprises an RFID tag 104 (e.g. operating in the UHF range) and an optical mark 106, for example a 1D or 2D code.

In the illustrated embodiment, the RFID tag 104 and the optical mark 106 are located on different parts of the medical container. For example, the RFID tag may be located on the cap 102 and the optical mark 106 may be located on the barrel 101, or conversely.

Alternatively, both the RFID tag 104 and the optical mark may be located on a same part of the medical container.

The data storage system may comprise a computer server and/or a storage drive. Advantageously, the data storage system may comprise several computer servers and/or several storage drives.

In the case of a storage drive, the manufacturer may transfer manufacturer processing data to the storage drive, and provide the storage drive to the customer. Hence, the customer may access the storage drive and review the data, thereby allowing him to check the conformity of the manufacturer processing with standards.

In the case of a computer server, the manufacturer may transfer manufacturer processing data to the server. The customer may then access the server and review the data, in particular for conformity check. The customer may also transfer customer processing data to the server.

The access to the data granted by the manufacturer to the customer may be total, meaning that the customer may access the full data stored in the storage data system, or partial, meaning that the customer may access only a part of the data stored in the storage data system.

Moreover, in addition to the review of the data, the customer may use these data and implement them in the customer chain.

According to a first embodiment, a computer server is shared between the manufacturer and the customer. The manufacturer and the customer may exchange data with each other.

According to a second embodiment, the manufacturer may access a first server, called manufacturer server, and the customer may access a second server, called customer server. The manufacturer may transfer manufacturer processing data to the manufacturer server, and transfer these data, or part of them, to the customer server. The customer may then access the customer server to review these data. The customer may transfer customer processing data to the customer server, and transfer these data, or part of them, to the manufacturer server.

An example of the computer server may be of a "cloud" type.

In practice, the processing of the medical containers may comprise the following steps:

A) Providing a material for manufacturing a plurality of medical containers.

B) Applying the RFID tag(s) and/or optical mark on and/or within the material of each medical container during the earliest steps of the manufacturing of the medical containers, said RFID tag(s) and/or optical mark storing and/or encoding a corresponding unique identifier for each respective medical container.

Manufacturing the medical containers may comprise at least one of the following steps: cutting, washing, forming glass canes or molding plastic materials which are used as a raw material for the medical container, printing a scale such as a volumetric scale, annealing the medical containers, washing the medical containers, applying a lubricant, assembling a tip including a needle onto the barrel of the medical containers, assembling a tip cap onto the barrel (or onto the needle if any), and visually inspecting the medical containers.

Even if the application of the RFID tag(s) and/or optical mark on or in the medical container may be implemented at any of the above manufacturing steps, said application is preferably implemented after the annealing step.

Advantageously, the RFID tag(s) and/or optical mark may be applied within the material of the medical container. Preferably, the application is performed as soon as possible in the manufacturing process, taking into account possible technical limitations (e.g. heat resistance of the RFID tag and/or optical mark). For example, if an optical mark is performed with a femtosecond laser, the marking is carried out after the annealing since the femtosecond laser marking would not sustain the annealing temperatures. However, in case of enamel sintering, the marking may be performed before annealing.

In an embodiment, an optical mark is laser-marked within the material of the medical container with a femtosecond laser. When a needle is intended to be assembled to the medical container, the marking is performed after the annealing but before the assembly of the needle, mainly because in that way, the marking is performed as early as possible, thereby allowing tracking the container transformations as early as possible.

C) Writing data relative to the manufacturing steps of the medical containers and/or individual physical data of each medical container in a data storage system, said written data being associated with the unique identifier of each respective medical container.

Step C) may be implemented during one or more manufacturing steps of the medical containers, preferably at each manufacturing step of the medical containers.

The data written in the data storage system may include (non-limitative list):

- data relative to the forming station: machine settings, dimensional control, date, manufacturing station identifier, external temperature, raw material batch number;
- data relative to the annealing step: annealing oven temperature profile, date, etc.;
- data relative to the needle assembly/intermediate packaging: type of glue used, gluing process key process input variables, cosmetic and dimensional control results;
- data relative to the inspection procedure; dimensional and cosmetic defects provided by a control apparatus, type of control apparatus;
- data relative to the cleaning step: type of cleaning fluid used, temperature of the cleaning fluid, cleaning time, number of cleaning cycles;
- data relative to the lubrication step: type of lubricant used, temperature of lubrication, flow rate of the lubricant, lubrication time.

Before step C), an additional comparison step may be implemented. Said comparison step enables comparing the data associated to the unique identifier of each medical container with a reference identifier in order to ensure that the compared medical container is the one sought, for instance the one identified on the manufacturing order. Whether the comparison step is negative, another comparison step may occur. Whether the comparison step is positive, step C) may be implemented.

In some embodiments, the processing of the medical containers may comprise the following steps:

D) Placing the medical containers into a nest.

E) Writing data relating to said subsequent processing step applied to the medical containers placed in the nest in the data storage system.

Said subsequent processing steps may be at least one of the following:

- sterilization of the nest and of each of the medical containers arranged in the nest;
- filling each medical container arranged in the nest with a pharmaceutical composition;
- stoppering each of the medical containers;
- conveying the nest to an inspection spot wherein each of the medical containers may be inspected;
- storing the nest into a tub for intermediate storage and/or shipment.

The above-mentioned steps may be implemented either at the manufacturer's place, or at the customer's place.

Advantageously, once the nest is arranged in a tub, a film may be placed to cover the upper opening of the tub containing the nest, so as to close the tub. The film may be in any appropriate material showing good mechanical resistance and sealing properties. Polyethylene films are particularly suited for that purpose, especially Tyvek® which is a nonwoven synthetic material made from polyethylene fibers.

The tubs may be placed into one or more header bags which are then sealed. The header bags may then be placed into cases which are labelled, and the cases may be placed onto pallets. The pallets may then be moved to a sterilization chamber in order to sterilize them. The sterilization is preferably performed with ethylene oxide or steam.

Step E) may be implemented during one or more processing steps of the medical containers, preferably at each processing step.

Typically, the data written in the data storage system at step E) may include (non-limitative list):

- data relative to the packaging station: type of apparatuses used, and preferably their settings, for carrying out the placement of the containers into the nest, the placement of the nest into the tub, and the placement of the tub into the header bag, date, manufacturing station identifier, external temperature, raw material batch number;
- data relative to the placement of the containers into the nest: features of the nest;
- data relative the filing station: type of apparatuses used, and preferably their settings, for carrying out the filing, date, filing station identifier, external temperature;
- data relative to the pharmaceutical composition: type of pharmaceutical composition, temperature, pressure, viscosity;
- data relative to the placement of the nest into the tub: features of the tub, features of the film such as the constitutive material of the film;
- data relative to the placement of the tub into the header bag: features of the header bag.

The pallets containing the medical containers may be transported to a secondary packaging plant.

Then, the medical containers may be removed from their nests and then packaged into a secondary packaging, for example the final packaging of each medical container, such as a cardboard box.

In some embodiments, an optical mark encoding the unique identifier of the medical container may be formed on or in the final, individual packaging of the medical container. For example, the medical container may be placed in a cardboard box after being filled, in view of being sent to the point of care. An optical mark such as a 1D or 2D code may be printed in the corresponding cardboard box. In this way, a user may read the unique identifier of the medical container even when it is enclosed in the cardboard box.

Thanks to the at least two elements (RFID tag(s) and/or optical mark) storing and/or encoding the unique identifier of each medical container according to different technologies, the unique identifier may be read by at least two different readers operating according to said technologies. In particular, during the industrial process, an UHF reader, which is frequently used in industrial facilities, may be used to track the medical containers. Then, at point of use, an NFC or an optical reader, which is more easily available for an end user (e.g. via a smartphone), may be used for reading the unique identifier of the medical container and accessing at least part of the data written in the data storage system. The combination of the RFID tag(s) and/or optical mark allows reading the unique identifier of the medical container at any stage of its lifetime, with a reader suited at this stage. Besides, at least in the industrial stage, the unique identifier may be read thanks to the first RFID tag even if the medical container is not visible, for example when it is enclosed in a packaging, or hidden by a layer of packaging or any object between the reader and the medical container.

The invention claimed is:

1. A medical container comprising:

a first RFID disposed on a first surface of the medical container, the first RFID tag being operable in a first frequency band and being configured for storing a unique identifier of the medical container, the unique identifier uniquely identifying the container, the first RFID tag configured for long-range interrogation during industrial processing of the medical container; and a second RFID tag disposed on a second surface of the medical container, the second RFID tag being operable in a second frequency band lower than the first frequency band and configured to store the unique identifier of the medical container, the second RFID tag configured for near-field interrogation at a point of use of the medical container, wherein, in response to reading the first RFID tag during production or inspection of the medical container, a data storage system is configured to associate the unique identifier with at least one of:

manufacturing parameters, inspection results, or environmental variables recorded during production of the medical container;

wherein the association of the unique identifier with said manufacturing parameters, inspection results, or environmental variables is only performed in response to reading the first RFID tag, and wherein manufacturing traceability data and point-of-use verification are enforced through different RFID tags operating at different stages of a medical container lifecycle.

2. The medical container according to claim 1, wherein the first and second RFID tags are separate physical components mounted at different locations on the container.

3. The medical container according to claim 1, further comprising an optical mark selected from at least one of: a tamper-resistant laser-etched mark; a chemically durable mark resistant to sterilization processes; or a redundant unique identifier readable in low-light conditions, wherein the optical mark comprises at least one of: a one-dimensional mark, a two-dimensional mark or a human readable text.

4. The medical container according to claim 3, wherein (i) the first RFID tag and (ii) the second RFID tag or the optical mark are located on different parts of the medical container, and wherein the second RFID tag serves a distinct function, at a different operational stage of the supply or clinical workflow, including at least one of patient-facing authentication, bedside verification, chain-of-custody tracking, or reduced-range secure access, distinct from the industrial tracking functions of the first RFID tag.

5. A system comprising:

at least one medical container according to claim 1; and a data storage system configured to store the unique identifier of each medical container in compliance with GS1 EPC Gen2 standards to ensure traceability, interoperability, and protection against identifier duplication or tampering.

6. The system according to claim 5, wherein the data storage system is further configured to associate each unique identifier with step-specific data recorded during manufacture, the step-specific data including one or more of: forming conditions, annealing parameters, needle assembly data, inspection outcomes, cleaning cycles, or lubrication timing.

7. The system according to claim 5, further comprising:

at least one first RFID reader coupled to the data storage system and configured to read the first RFID tag of each medical container; and at least one of:

(i) a second RFID reader coupled to the data storage system and configured to read the second RFID tag of each medical container, the second RFID reader being optimized for near-field scanning at clinical endpoints; and (ii) an optical reader coupled to the data storage system and configured to read the optical mark of each medical container, the optical reader comprising a scanner operable in low-light environments.

8. The system according to claim 5, wherein the data storage system is configured to automatically update or append process data for each medical container as it progresses through sequential manufacturing stages, thereby enabling continuous traceability.

9. A method for tracking data relating to at least one medical, comprising:

providing at least one medical container according to claim 1;

generating the unique identifier of each medical container;

forming the first RFID tag on each medical container, wherein the first RFID tag stores the unique identifier of the respective medical container;

forming on each medical container at least one of the second RFID tag storing the unique identifier of the respective medical container or the optical mark encoding the unique identifier of the respective medical container, the second RFID tag being configured for storing the unique identifier of the medical container, wherein the second RFID tag is optimized for point-of-use scanning, while the first RFID tag is optimized for industrial tracking;

storing, in a data storage system, the unique identifier of each medical container in association with one or more of manufacturing parameters, inspection results, or environmental variables recorded during production of the medical container.

10. The method according to claim 9, wherein forming the first and/or second RFID tag comprises at least one of: labelling, in-mold labelling, screwing, over-molding, or direct antenna printing.

11. The method according to claim 9, wherein forming the optical mark comprises at least one of: labelling, in-mold labelling, enamel sintering, inkjet printing, laser marking, including picosecond laser marking or femtosecond laser marking, drop-on demand printing, or dot peen marking.

12. The method according to claim 9, further comprising:

(a) providing:

at least one first RFID reader coupled to the data storage system and configured to read the first RFID tag of each medical container; and at least one of:

(i) a second RFID reader coupled to the data storage system and configured to read the second RFID tag of each medical container; and (ii) an optical reader coupled to the data storage system and configured to read the optical mark of each medical container; and (b) reading at least one of the first RFID tag, the second RFID tag and the optical mark of at least one medical container with the first RFID reader, the second RFID reader and/or the optical reader and determining from the data storage system the unique identifier of said at least one medical container.

13. The method according to claim 9, further comprising: using the second RFID tag for point-of-care authentication or patient administration; and using the first RFID tag for logistics or warehouse management.

14. The medical container of claim 1, wherein the second RFID tag is positioned on an externally accessible surface of the container to facilitate handheld reader access, and the first RFID tag is located in an embedded or internal region suitable for automated equipment scanning.

15. The medical container of claim 1, wherein the near-field environment comprises at least one of: a patient bedside, a nurse station, or a medication dispensing terminal, and wherein the industrial environment comprises at least one of: an automated inventory system, a logistics checkpoint, or a bulk container storage area.

16. The medical container according to claim 1, wherein the second RFID tag is embedded within a barrel portion of the container, and the first RFID tag is disposed on an exterior surface of a removable cap of the container.

17. The medical container according to claim 1, wherein the data storage system records, in association with the unique identifier, at least one of:

manufacturing station identifiers, process temperature profiles, lubrication parameters, inspection defect data, or cleaning cycle information of the medical container.

* * * * *